US 8,721,553 B2

(12) United States Patent
Lee et al.

(10) Patent No.: US 8,721,553 B2
(45) Date of Patent: May 13, 2014

(54) FLUID-FILLABLE ULTRASOUND IMAGING CATHETER TIPS

(75) Inventors: Warren Lee, Niskayuna, NY (US); Douglas Glenn Wildes, Ballston Lake, NY (US); Weston Blaine Griffin, Niskayuna, NY (US); Reinhold Bruestle, Zipf (AT)

(73) Assignee: General Electric Company, Niskayuna, NY (US)

( * ) Notice: Subject to any disclaimer, the term of this patent is extended or adjusted under 35 U.S.C. 154(b) by 1238 days.

(21) Appl. No.: 12/104,223

(22) Filed: Apr. 16, 2008

(65) Prior Publication Data

US 2008/0287797 A1 Nov. 20, 2008

Related U.S. Application Data

(60) Provisional application No. 60/917,995, filed on May 15, 2007.

(51) Int. Cl.
*A61B 8/14* (2006.01)
*G01S 15/00* (2006.01)

(52) U.S. Cl.
USPC .............................................. 600/466; 73/633

(58) Field of Classification Search
USPC ............................................ 600/466; 73/633
See application file for complete search history.

(56) References Cited

U.S. PATENT DOCUMENTS

| | | | | |
|---|---|---|---|---|
| 4,649,925 A * | 3/1987 | Dow et al. | | 600/446 |
| 5,085,221 A * | 2/1992 | Ingebrigtsen et al. | | 600/446 |
| 5,176,141 A * | 1/1993 | Bom et al. | | 600/467 |
| 5,240,003 A * | 8/1993 | Lancee et al. | | 600/467 |
| 5,375,602 A * | 12/1994 | Lancee et al. | | 600/463 |
| 5,560,362 A * | 10/1996 | Sliwa et al. | | 600/439 |
| 5,596,991 A * | 1/1997 | Tanaka | | 600/459 |
| 5,611,343 A | 3/1997 | Wilson | | |
| 6,036,646 A * | 3/2000 | Barthe et al. | | 600/459 |
| 6,120,452 A * | 9/2000 | Barthe et al. | | 600/459 |
| 6,171,247 B1 | 1/2001 | Seward et al. | | |
| 6,306,096 B1 | 10/2001 | Seward et al. | | |
| 6,425,870 B1 | 7/2002 | Flesch | | |
| 7,285,116 B2 * | 10/2007 | de la Rama et al. | | 606/27 |
| 7,431,698 B2 * | 10/2008 | Bruestle | | 600/459 |
| 7,491,172 B2 * | 2/2009 | Bruestle | | 600/459 |
| 7,494,469 B2 * | 2/2009 | Bruestle | | 600/459 |
| 7,666,143 B2 | 2/2010 | Wilser et al. | | |

(Continued)

FOREIGN PATENT DOCUMENTS

| | | | |
|---|---|---|---|
| JP | 57013001 U1 | 1/1982 | |
| JP | 10262972 A | 10/1998 | |

(Continued)

*Primary Examiner* — Long V. Le
*Assistant Examiner* — Angela M Hoffa
(74) *Attorney, Agent, or Firm* — Fletcher Yoder, P.C.

(57) ABSTRACT

An imaging catheter tip is presented. The imaging catheter tip includes a housing. Further, the imaging catheter tip includes a transducer assembly located within the housing in a distal portion of the imaging catheter tip. The transducer assembly includes a transducer. In addition, the imaging catheter tip includes a motor located within the housing in a proximal portion of the imaging catheter tip. The motor is configured to facilitate oscillation of the transducer assembly about a longitudinal axis of the imaging catheter tip. The imaging catheter tip also includes a fill tube disposed between the motor and the housing. The fill tube is configured to deliver acoustic coupling fluid to the distal portion of the imaging catheter tip.

25 Claims, 5 Drawing Sheets

(56) References Cited

U.S. PATENT DOCUMENTS

| | | | |
|---|---|---|---|
| 7,699,782 B2 * | 4/2010 | Angelsen et al. | 600/444 |
| 8,038,619 B2 * | 10/2011 | Steinbacher | 600/444 |
| 2003/0055338 A1 | 3/2003 | Steininger et al. | |
| 2005/0124899 A1 * | 6/2005 | Byrd et al. | 600/467 |
| 2005/0154312 A1 * | 7/2005 | Bruestle | 600/459 |
| 2005/0203416 A1 * | 9/2005 | Angelsen et al. | 600/463 |
| 2007/0167813 A1 | 7/2007 | Lee et al. | |
| 2007/0167821 A1 | 7/2007 | Lee et al. | |
| 2007/0167824 A1 | 7/2007 | Lee et al. | |
| 2007/0167825 A1 | 7/2007 | Lee et al. | |
| 2007/0167826 A1 | 7/2007 | Lee et al. | |
| 2008/0285824 A1 | 11/2008 | Wildes et al. | |

FOREIGN PATENT DOCUMENTS

| | | | |
|---|---|---|---|
| JP | 2006167465 A | | 6/2006 |
| JP | 2006229174 A | * | 8/2006 |
| WO | 2005096266 A1 | | 10/2005 |

* cited by examiner

FLUID-FILLABLE ULTRASOUND IMAGING CATHETER TIPS

CROSS REFERENCE TO RELATED APPLICATIONS

This application claims priority to U.S. Provisional Patent Application No. 60/917,995, entitled "SELF-CONTAINED, FLUID-FILLABLE REAL-TIME THREE-DIMENSIONAL ULTRASOUND IMAGING CATHETER TIPS," filed May 15, 2007, which is herein incorporated by reference in its entirety for all purposes.

BACKGROUND

The present disclosure relates generally to ultrasound imaging and, more particularly, to imaging catheter tips which contain acoustic transducers for obtaining ultrasound images.

Acoustic transducers have found application in medical imaging where an acoustic probe is held against a patient and the probe transmits and receives ultrasound waves. The received energy may, in turn, facilitate the imaging of the tissues of the patient. For example, transducers may be employed to image the heart of the patient.

Catheter-based ultrasonic imaging techniques are interventional procedures that generally involve inserting a probe, such as an imaging catheter, into a vein, such as the femoral vein, or an artery. As will be appreciated, catheter-based ultrasonic imaging techniques may be employed for imaging the heart, such as when monitoring and/or directing treatment of atrial fibrillation. Consequently, it is highly desirable that transducer assemblies used in catheters be capable of two-dimensional and/or real-time three-dimensional imaging. Such applications are quite demanding, requiring very small transducer packages that can nevertheless collect large amounts of information.

However, it may be difficult to provide a transducer package that is mechanically, acoustically, and electrically suitable. Therefore, it may be desirable to provide a transducer probe assembly suitable for interventional imaging that has acceptable mechanical, electrical, and/or acoustic characteristics.

BRIEF DESCRIPTION

Briefly, in accordance with aspects of the present technique, an imaging catheter tip is presented. The imaging catheter tip includes a housing. Further, the imaging catheter tip includes a transducer assembly located within the housing in a distal portion of the imaging catheter tip. The transducer assembly includes a transducer. In addition, the imaging catheter tip includes a motor located within the housing in a proximal portion of the imaging catheter tip. The motor is configured to facilitate oscillation of the transducer assembly about a longitudinal axis of the imaging catheter tip. The imaging catheter tip also includes a fill tube disposed between the motor and the housing. The fill tube is configured to deliver acoustic coupling fluid to the distal portion of the imaging catheter tip.

In accordance with further aspects of the present technique, another imaging catheter tip is presented. The imaging catheter tip includes a housing. Further, the imaging catheter tip includes a transducer located within the housing in a distal portion of the imaging catheter tip. In addition, the imaging catheter tip includes a motor assembly located within the housing in a proximal portion of the imaging catheter tip. The motor assembly includes a motor holder and a motor configured to facilitate oscillation of the transducer about a longitudinal axis of the imaging catheter tip. The imaging catheter tip also includes a flexible interconnect cable disposed between the motor assembly and the housing. The flexible interconnect cable is configured to connect to the transducer.

In accordance with further aspects of the present technique, a method of using an imaging catheter tip is presented. The method includes filling a distal portion of the imaging catheter tip with acoustic coupling fluid from a proximal end of the imaging catheter tip using a fill tube. The method also includes inserting the imaging catheter tip into a patient. The method further includes collecting ultrasound imaging data using a transducer assembly disposed in the distal portion of the imaging catheter tip.

In accordance with yet another aspect of the present technique, a method of initializing the oscillation of a transducer assembly within an imaging catheter tip is presented. The method includes rotating the transducer assembly in a first rotational direction about an axis of rotation until a hard stop is contacted. The method also includes determining a first rotational location indicative of the location of the hard stop. The method further includes rotating the transducer assembly about the axis of rotation based on at least the first rotational location.

In accordance with further aspects of the present technique, a system is presented that includes an imaging system for collecting imaging data and an imaging catheter. The imaging catheter includes an imaging catheter tip. The imaging catheter tip includes a transducer assembly located in a distal portion of the imaging catheter tip. The imaging catheter tip also includes a motor assembly located in a proximal portion of the imaging catheter tip. In addition, the imaging catheter tip includes a fill tube configured to fill the distal portion of the imaging catheter tip with fluid from a proximal end of the imaging catheter tip.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
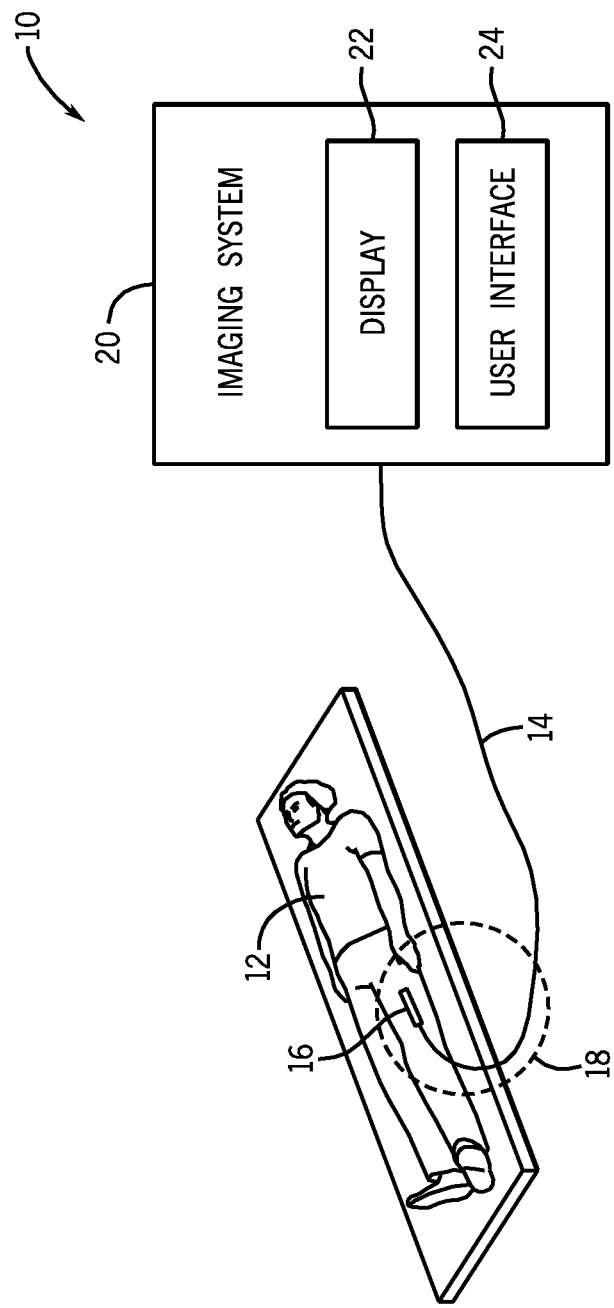
FIG. 1 is a block diagram of an exemplary ultrasound imaging system, in accordance with aspects of the present technique.

Imaging probes containing transducer assemblies for obtaining real-time, three-dimensional ultrasound imaging may use a motor assembly to oscillate transducer assemblies about an axis of the imaging probe. In doing so, the transducer assemblies may be capable of obtaining real-time, three-dimensional ultrasound images by sweeping a two-dimensional slice through a three-dimensional volume. Acoustic coupling fluid may be used in conjunction with the transducer assemblies to provide an effective or suitable acoustic transition between the transducer and the surrounding housing. Such imaging probes are typically filled with acoustic coupling fluid at the time of manufacture. Such imaging probes also typically include a fluid barrier to separate the motor from the fluid-filled space that houses the transducer. The barrier is penetrated by a driveshaft that couples the motor to the moving transducer. A fluid seal on the driveshaft prevents or minimizes the leakage of fluid from the transducer space to the motor space.

When the imaging probe is a catheter tip or other very small device intended for imaging in space-constrained regions, the space constraints may preclude isolating the motor from the fluid-filled transducer space. In such scenarios, the presence of the acoustic coupling fluid in the imaging catheter tip for long periods of time before use may prove problematic. For instance, the fluid may gradually seep into the motor and associated gearbox, increasing the risk of performance degradation. For similar reasons, the risk of shelf-life failures may be increased. Also, corrosion and leaching may occur since the fluid is encased in the imaging catheter tip for such a long period of time. Furthermore, sterilization may be more difficult when filling the imaging catheter tip at the time of manufacture. These problems may all result in reduced performance of the imaging catheter.

Other problems may be introduced depending on the methods used to fill the imaging catheter tip. For instance, many imaging catheter tips are filled from the distal end of the imaging catheter tip. This may prove problematic in that the imaging catheter tip may not be properly sealed after filling. In addition, many typical methods for filling the imaging catheter tip have a tendency to generate bubbles in the acoustic coupling fluid which can cause problems during image data collection.

Another problem sometimes encountered with these imaging catheter tips is that the interconnect cabling used to send and receive electrical signals between the transducer assembly and an external imaging system tends to be somewhat stiff. When the transducer assembly is rotated by the motor assembly, this stiffness may exert undue torque on the motor assembly. This requires extra power from the motor and can ultimately generate excessive temperatures within the imaging catheter tip.

With the foregoing in mind, using the present technique, the aforementioned limitations may be overcome by using an imaging catheter tip with a transducer assembly capable of real-time, three-dimensional imaging for use in an invasive probe employed in space critical applications such as intracardiac imaging. The system and methods presented allow for filling of the imaging catheter tip with acoustic coupling fluid at the time of use. The imaging catheter tip incorporates fill and vent tubes and other specific features which may minimize trapped bubbles in the imaging catheter tip during fluid filling. The imaging catheter tip may also include one or more hard stop mechanisms allowing for multiple ranges of oscillatory motion of the transducer assembly. In addition, the imaging catheter tip may allow for an increased length of the rotatable interconnect cable, reducing the torque, power, and temperature requirements of the motor assembly used to oscillate the transducer assembly.

There may be numerous technical advantages associated with the present technique of filling the imaging catheter tip at the time of use. For one, filling at the time of use may reduce the risk of performance degradation associated with fluid incursion into the motor and associated gearbox as compared to filling at the time of manufacture. Since the acoustic coupling fluid may be introduced into the imaging catheter tip only a short while before use, there may be considerably less chance of the fluid leaking into these components to such a degree that their performance will be adversely affected. For similar reasons, the risk of shelf-life failures due to fluid-component interactions may also be reduced. Techniques for packaging and automatically filling imaging catheter tips as described herein are related in the US Patent Application entitled "PACKAGING AND FLUID FILLING OF ULTRASOUND IMAGING CATHETERS," filed Apr. 16, 2008 by Warren Lee et al., which is herein incorporated by reference in its entirety for all purposes.

Furthermore, the present technique may cause improved biocompatibility due to the fact that there may be less time for leaching and corrosion to occur. In a similar manner, there may be less diffusion, both of the acoustic coupling fluid out of the imaging catheter tip and of gases into the imaging catheter tip and acoustic coupling fluid. In addition, sterilization may be easier using the present technique since ethylene oxide gas sterilization may be utilized. Also, the fact that the distal tip may be closed, compared to a design requiring filling from the distal end, may lead to increased safety. Another advantage may include the ability to integrate the imaging catheter tip with any manufacturer's catheter due to the self-contained nature of the imaging catheter tip.

With the foregoing general discussion in mind, specific implementations of the present technique are discussed below. FIG. 1 is a block diagram of an exemplary system 10 for use in ultrasound imaging, in accordance with aspects of the present technique. As will be appreciated by those skilled in the art, the figures are for illustrative purposes and are not necessarily drawn to scale. The system 10 may be configured to facilitate acquisition of ultrasound image data from a patient 12 via an imaging catheter 14. For example, the imaging catheter 14 may be configured to acquire ultrasound image data representative of a region of interest in the patient 12. In accordance with aspects of the present technique, the imaging catheter 14 may be configured to function as an invasive probe. It should also be noted that, although the embodiments illustrated are described in the context of a catheter-based probe, other types of invasive probes such as endoscopes, laparoscopes, surgical probes, transrectal probes, transvaginal probes, intracavity probes, probes adapted for interventional procedures, or combinations thereof are also contemplated in conjunction with the present technique. Reference numeral 16 is representative of a portion of the imaging catheter 14 disposed inside the patient 12, such as inserted into a vein. Reference numeral 18 is indicative of a portion of the imaging catheter 14 depicted in greater detail in FIG. 2.

The system 10 may also include an ultrasound imaging system 20 that is in operative association with the imaging catheter 14 and configured to facilitate acquisition of ultrasound image data. It should be noted that although the exemplary embodiments illustrated hereinafter are described in the context of a medical imaging system, such as an ultrasound imaging system, other imaging systems and applications are also contemplated (e.g., industrial applications, such as non-destructive testing, borescopes, and other applications where ultrasound imaging within confined spaces may be used). Additionally, the exemplary embodiments illustrated and described hereinafter may find application in multi-modality imaging systems that employ ultrasound imaging in conjunction with other imaging modalities, position-tracking systems, or other sensor systems.

Further, the ultrasound imaging system 20 may be configured to display an image representative of a current position of the imaging catheter 14 within the patient 12. As illustrated in FIG. 1, the ultrasound imaging system 20 may include a display area 22 and a user interface area 24. In accordance with aspects of the present technique, the display area 22 of the ultrasound imaging system 20 may be configured to display a two- or three-dimensional image generated by the ultrasound imaging system 20 based on the image data acquired via the imaging catheter 14. For example, the display area 22 may be a suitable CRT or LCD display on which ultrasound images may be viewed. The user interface area 24 may include an operator interface device configured to aid the operator in identifying a region of interest to be imaged. The operator interface may include a keyboard, mouse, trackball, joystick, touch screen, or any other suitable interface device.

Figure 2:
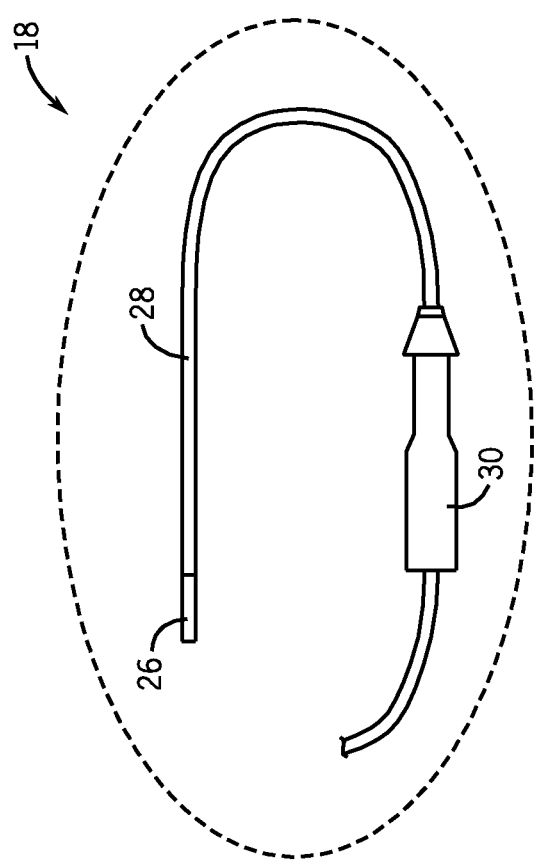
FIG. 2 is a side view of a portion of an invasive probe including an exemplary imaging catheter tip and transducer assembly for use in the system illustrated in FIG. 1, in accordance with aspects of the present technique.

FIG. 2 illustrates an enlarged view of the portion 18 (see FIG. 1) of the imaging catheter 14 (see FIG. 1). As depicted in FIG. 2, the imaging catheter 14 may include a tip 26 on the distal end of a flexible shaft 28. It is this distal tip 26 that houses the transducer assembly and motor assembly as discussed herein. The imaging catheter 14 may also include a handle 30 configured to facilitate an operator manipulating the flexible shaft 28. In the context of this disclosure, points within the imaging catheter 14 which are closer to the handle 30 may be referred to as proximal whereas points within the imaging catheter which are further from the handle 30 may be referred to as distal. The distance between the transducer assembly and the handle 30 may be in a range from about 10 cm to about 150 cm depending on the type of probe and application.

Figure 3:
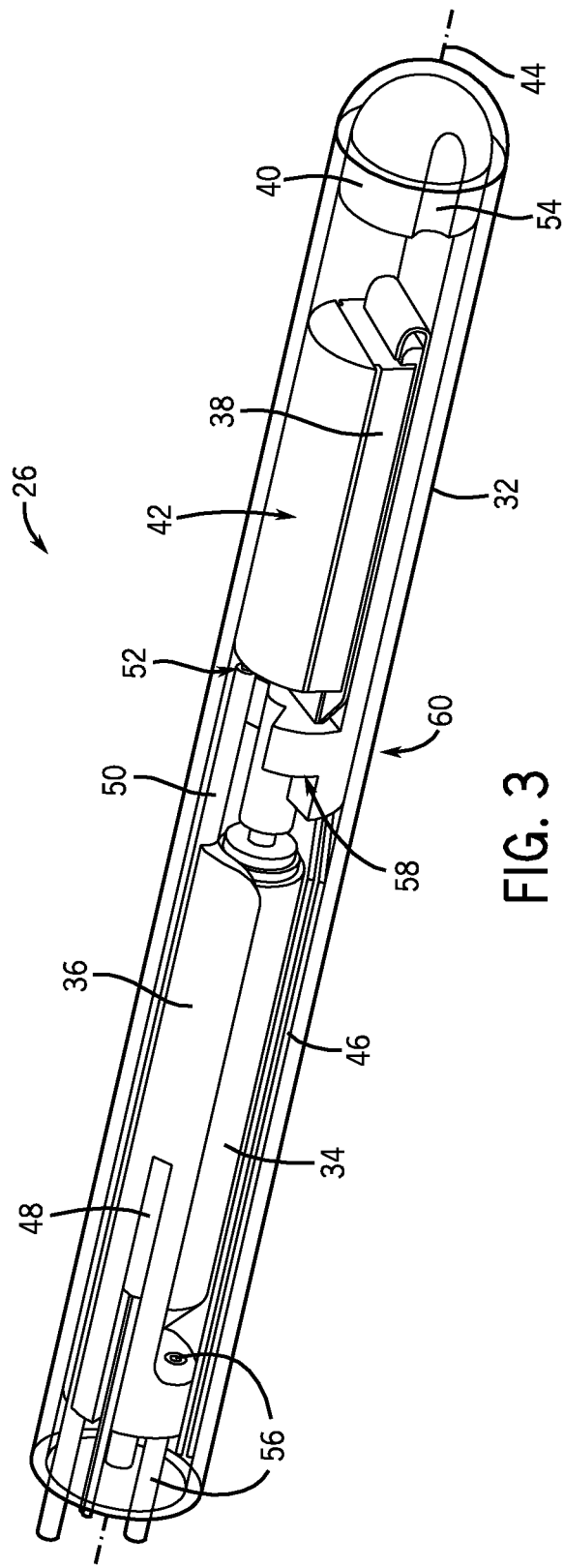
FIG. 3 is a perspective side view of an exemplary embodiment of an imaging catheter tip, in accordance with aspects of the present technique.

FIG. 3 depicts an exemplary embodiment of an imaging catheter tip 26. In the illustrated embodiment, the imaging catheter tip 26 includes a housing 32 which contains, among other things, a motor 34, a motor holder 36, a transducer 38, and a transducer holder 40, and, optionally, a lens 42. Similar imaging catheter tips are described in U.S. Patent Application Publication Nos. 2007/0167813 filed on Jan. 18, 2007, 2007/0167821 filed on Nov. 30, 2005, 2007/0167824 filed on Jan. 11, 2006, 2007/0167825 filed on Jan. 11, 2006, and 2007/0167826 filed on Jan. 11, 2006, each to Warren Lee et al. as well as U.S. patent application Ser. No. 12/099,862 filed Apr. 9, 2008 to Warren Lee et al., each of which is incorporated herein by reference in its entirety for all purposes. The motor 34 may be used to oscillate the transducer 38 about an axis 44. The transducer 38 may, for example, be a 64-element phased array and may be oscillated about the axis 44 in order to generate real-time, three dimensional imaging by sweeping a two-dimensional slice over a three-dimensional volume. The motor 34 may be controlled by a motor controller external to the imaging catheter tip 26. For example, the motor controller may be incorporated as part of the handle 30 or ultrasound imaging system 20. The motor 34 may, in certain embodiments, be configured for low torque and low speeds since the motor 34 may only be required to oscillate the transducer 38 through a limited range of angular motion, for instance, 90-180 degrees of rotation. However, the motor 34 may also be a high-precision motor in that the imaging carried out by the transducer 38 and associated lens 42 may require precise oscillation.

In the illustrated embodiment, the motor holder 36 may serve several purposes with respect to the motor 34. First, the motor holder 36 may serve to fix the motor in a specific position (e.g. centered relative to axis 44). Second, the motor holder 36 may serve to support or constrain other components of the imaging catheter tip 26. For instance, as shown in FIG. 3, the motor holder 36 may support a thermistor 48, a fill tube 50, a vent tube 56, the proximal end of the flexible interconnect cable 46, and other components. Further, the motor holder 36 may serve as a bulkhead to minimize the adverse effects of an acoustic coupling fluid filling back into the proximal portion of the imaging catheter tip 26. In addition, the motor holder 36 may act as protection for other components within and outside the imaging catheter tip 26 from the motor 34. For instance, the motor 34 may generate heat even from the minimal oscillations required for imaging. The motor holder 36 may be made of a material with a high thermal conductivity, to help distribute the motor heat over a greater length of the imaging catheter tip 26. In some embodiments, the motor holder 36 may be made of a material with a low thermal conductivity, to minimize the transfer of heat from the motor 34 to the housing 32, where it could create hot spots that could potentially be injurious to a patient. In other embodiments, the motor holder 36 may be made of an anisotropic or composite material with high thermal conductivity in a longitudinal direction (e.g., parallel to axis 44) and low thermal conductivity in transverse directions (e.g., radial to the imaging catheter 14 or perpendicular to axis 44) so as to both distribute heat along the imaging catheter tip 26 and reduce direct transfer of heat to the catheter housing 32.

A thermistor 48 may be used to monitor the temperature of the motor 34 and motor holder 36. The thermistor 48 may send information to the ultrasound imaging system 20 which may, in turn, take appropriate actions when the thermistor 48 senses that the internal temperature of the imaging catheter tip 26 has reached a predetermined level. For instance, the ultrasound imaging system 20 may automatically place restrictions on how fast subsequent imaging may take place. By restricting the ultrasound imaging system 20 in such a way, subsequent heat generation may be minimized. Alternatively, the ultrasound imaging system 20 may report to the operator of the ultrasound imaging system 20 that excessive temperatures have been reached. In this manner, the operator may take appropriate corrective measures.

Using the present technique, the imaging catheter tip 26 may be filled with acoustic coupling fluid at or near the time of use of the imaging catheter tip 26. For instance, the imaging catheter tip 26 may be filled during or immediately prior to an examination in which the imaging catheter tip 26 is used to collect imaging data. In other words, the imaging catheter tip 26 may be filled at the examination site such as at a clinic, hospital, or doctor's office. For example, the imaging catheter tip 26 may be filled within a certain number of hours (e.g., one, two, ..., eight, or twelve hours, and so forth) before use. Regardless of the specific time of filling, the imaging catheter tip 26 of the present technique is typically filled after manufacture and shipping of the imaging catheter tip 26.

In the illustrated embodiment, a fill tube 50 may be used to deliver an acoustic coupling fluid into a distal portion of the imaging catheter tip 26 from the proximal end of the imaging catheter tip 26 at or near the time of use of the imaging catheter tip 26. If an acoustically suitable coupling fluid is utilized, it may be possible to exclude the lens 42 and use only the transducer 38 for imaging. Advantages of excluding the lens 42 may include a more simplified design, greater signal-to-noise ratio due to less lens attenuation, and less friction with which to load the motor 34. Such an acoustic coupling fluid may have one or more of the following properties: (1) sound velocity and density similar to water, (2) low tendency for releasing gas (in order to minimize bubbles from forming after filling), (3) biocompatibility, (4) the ability to wet the inner surfaces of the imaging catheter tip 26, and so forth.

Several fluids have been tested and identified as possible candidates for the acoustic coupling fluid. These fluids include: (1) propylene glycol, (2) water, (3) ethanol, (4) polyethylene glycol, (5) 3M FC-3283 Fluorinert, and so forth. Other fluids may also prove suitable as this list is merely meant to be illustrative.

The acoustic coupling fluid may be introduced by the fill tube 50 at the fill port 52. In the illustrated embodiment, the fill port 52 may be located near the proximal end of the transducer holder 40. In one embodiment, the distal portion of the imaging catheter tip 26 is filled while the distal end of the imaging catheter tip 26 is pointing downward. In such an embodiment, the acoustic coupling fluid may fill the distal portion of the imaging catheter tip 26 through capillary action between the transducer 38 (and lens 42, if used) and the housing 32 of the imaging catheter tip 26. The acoustic coupling fluid may fill the distal portion of the imaging catheter tip 26 until the entire portion is filled.

In one embodiment, the fill tube 50 may be a metal tube or other rigid tube that may function as part of the hard stop mechanism, as discussed in greater detail below. However, through the flexible shaft 28 of the imaging catheter 14, the fill tube 50 may be required to be somewhat flexible. Therefore, the fill tube 50 may be a combination of a rigid tube in the imaging catheter tip 26 coupled to a long, flexible tube through the flexible shaft 28. Within the flexible shaft 28, the fill tube 50 may be a discrete tube inserted into a larger lumen in the catheter. Alternatively, the fill tube 50 may be one, or possibly more, lumens integrated into the catheter construction. However, with either design, the fill tube 50 provides a leak-tight, pressure-capable connection to the imaging catheter tip 26 and the fill port 52.

As the acoustic coupling fluid is introduced into the distal portion of the imaging catheter tip 26 in the depicted embodiment, bubbles may develop in the acoustic coupling fluid. However, in the illustrated embodiment, a vent 54 may be used at the distal end of the transducer holder 40. This vent 54 may facilitate the removal of the bubbles. It may also be possible for the operator of the imaging catheter tip 26 to use a simple "lasso" motion to force the bubbles to be removed through a vent tube 56 in response to centripetal forces. In other words, the vent 54 and vent tube 56 give the bubbles a route through which to exit the imaging catheter tip 26. The vent tube 56, which may receive expelled air and excess acoustic coupling fluid from the imaging catheter tip 26, may be similar to the fill tube 50 or may also be part of a lumen in the catheter. The vent tube 56 should also be leak-tight, but does not necessarily have to be able of sustaining high pressures, depending on the embodiment. In other embodiments, the expelled air and excess acoustic coupling fluid may simply pass around the other components in the imaging catheter tip 26, such as the signal cables and wiring.

In order to reduce the movement of the acoustic coupling fluid out of the distal portion of the imaging catheter tip 26 after filling, it may be possible to close one or both of the fill tube 50 and the vent tube 56. One of these tubes being closed may be enough to stop the flow of acoustic coupling fluid out of the distal end while still allowing the other tube to act as an expansion chamber during operation of the imaging catheter tip 26 as the acoustic coupling fluid heats up. In other embodiments, however, both tubes 50 and 56 may be closed.

Figure 4:
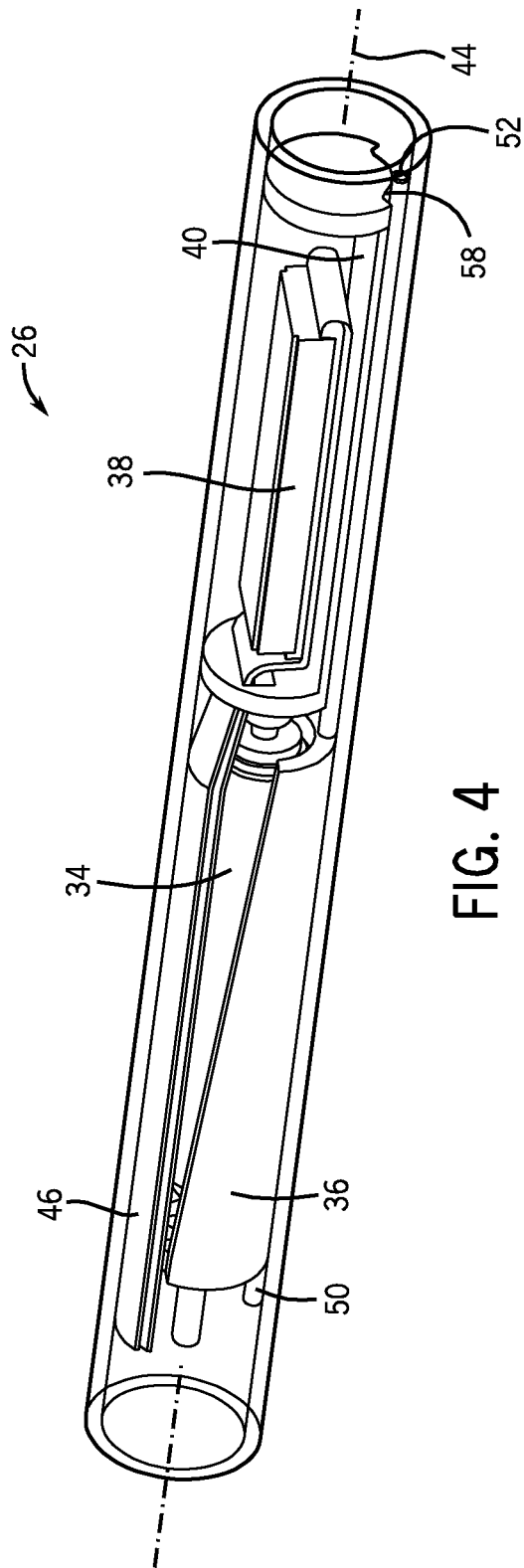
FIG. 4 is a perspective side view of another exemplary embodiment of an imaging catheter tip, in accordance with aspects of the present technique.

While FIG. 3 depicts one possible placement of the fill tube 50, FIG. 4 is a perspective side view of another exemplary embodiment of an imaging catheter tip 26. This illustrated embodiment is conceptually similar to the embodiment shown in FIG. 3. However, in this embodiment, the fill tube 50 may extend to the distal end of the imaging catheter tip 26.

When the distal tip is pointed downward and the acoustic coupling fluid is introduced through the fill port 52, the acoustic coupling fluid may fill the imaging catheter tip 26 from the distal end to the proximal end of the imaging catheter tip 26. In doing so, the chance of experiencing bubbles or air pockets may be reduced as compared to embodiments where the acoustic coupling fluid is introduced proximal to the transducer holder 40.

In addition, using the present technique, the imaging catheter tip 26 may use the fill tube 50 as part of a hard stop mechanism for calibrating the oscillation of the transducer 38. Returning now to FIG. 3, the transducer holder 40 may include a rotation constraint 58. In the depicted embodiment, the fill tube 50 may be used to initialize the rotational position of the transducer 38. The motor 34 may initially rotate the transducer holder 40 (and attached transducer 38) so that an arm of the rotation constraint 58 contacts the fill tube 50, which acts as a hard stop preventing further rotation in the initial direction. At this point, the rotational direction may be reversed and the transducer 38 may be rotated back by a known angle in order to center the transducer 38. Alternatively, after contacting the fill tube 50, the rotational direction may be reversed until an opposing arm of the rotation constraint 58 contacts the fill tube 50 again, at which point the rotational direction may be rotated back by a known angle until the transducer 38 is centered. The contact location may be used by software or mechanical means to center the transducer about the axis 44 of rotation relative to the fill tube 50. The angle that the rotation constraint 58 forms may determine the rotational limits for the transducer 38.

As illustrated, more than one set of rotational limits may be incorporated into the rotation constraint 58 by incorporating different constraint arms having different angular ranges. In such an embodiment, the fill tube 50 may be retracted or extended such that the desired set of constraint arms impact the fill tube 50. For example, it may be possible to retract the fill tube 50 in order to allow a wide angle rotation constraint 58 to contact the fill tube 50, thereby obtaining a larger rotational range limit (e.g. 180 degrees) which may, in turn, enable a greater field of view for the three-dimensional imaging. In addition, it may also be possible to initialize the rotational position of the transducer 38 without the use of a rotation constraint 58 mechanism. For instance, it may be possible to use sensors, such as a Hall sensor or optical sensor, to sense the rotational position and initialize the rotation in this manner.

Returning to FIG. 4, in this depicted embodiment the fill tube 50 may again act in conjunction with the rotation constraint 58 of the transducer holder 40 to fix the rotational limits of the transducer holder 40 and, therefore, the transducer 38. However, in the illustrated embodiment, the rotation constraint 58 and the fill tube 50 may interact at the distal end of the imaging catheter tip 26. In such an embodiment, the transducer holder 40 may be modified in such a way that a semi-annular pocket exists through which the fill tube 50 may extend. The edges of the semi-annular pocket in the transducer holder 40 which contact the fill tube 50 may then provide the rotational limits.

In addition, using the present technique, the imaging catheter tip 26 may allow for reduced torque on the motor 34. Returning now to FIG. 3, the motor 34 may be located near the transducer 38 and associated lens 42 in order to reduce the overall stiff length of the imaging catheter tip 26. Using the present technique, locating the motor 34 proximate to the transducer 38 may allow the imaging catheter 14 to be more maneuverable within confined spaces.

As discussed above, the flexible interconnect cable 46 may be used to send and receive electrical signals between the ultrasound imaging system 20 and the transducer 38 during imaging. Although the flexible interconnect cable 46 may be a flex circuit, it may also be a ribbon cable, discrete wires, or any other suitable conductive media which allows communication of electrical signals between the transducer 38 and the ultrasound imaging system 20. The flexible interconnect cable 46 may extend from the proximal end of the imaging catheter tip 26 to the transducer 38.

As discussed above, the flexible interconnect cable 46 attached to the transducer 38 may exert torque that is overcome by the motor 34 in order to oscillate the transducer 38. This torque is exerted because the flexible interconnect cable 46 exhibits a certain degree of stiffness. As described above, this torque effect may be minimized using the present technique in that spacing around the motor 34 may accommodate the motion of the flexible interconnect cable 46 as the transducer 38 oscillates. Also, in order to further increase the flexibility of the flexible interconnect cable 46, slits may be cut into the flexible interconnect cable 46 in the direction of the axis 44. However, there may still be a certain degree of stiffness generated by the flexible interconnect cable 46.

A semi-annular space around the motor 34 and motor holder 36, over all or part of the length of the motor 34, may provide room for the flexible interconnect cable 46 to translate and rotate with the oscillating transducer 38. In one embodiment, the flexible interconnect cable 46 may be constrained at the point 60 where the flexible interconnect cable 46 interfaces with the transducer holder 40 such that the flexible interconnect cable 46 may move proximal from the point 60, but not on the distal side of the point 60. In other words, in this embodiment, the portion of the flexible interconnect cable 46 proximal to point 60 may be unconstrained to a certain degree to accommodate oscillation of the transducer 38 while the portion of the flexible interconnect cable 46 distal to point 60 may be constrained by attachment to the transducer holder 40.

Figure 5:
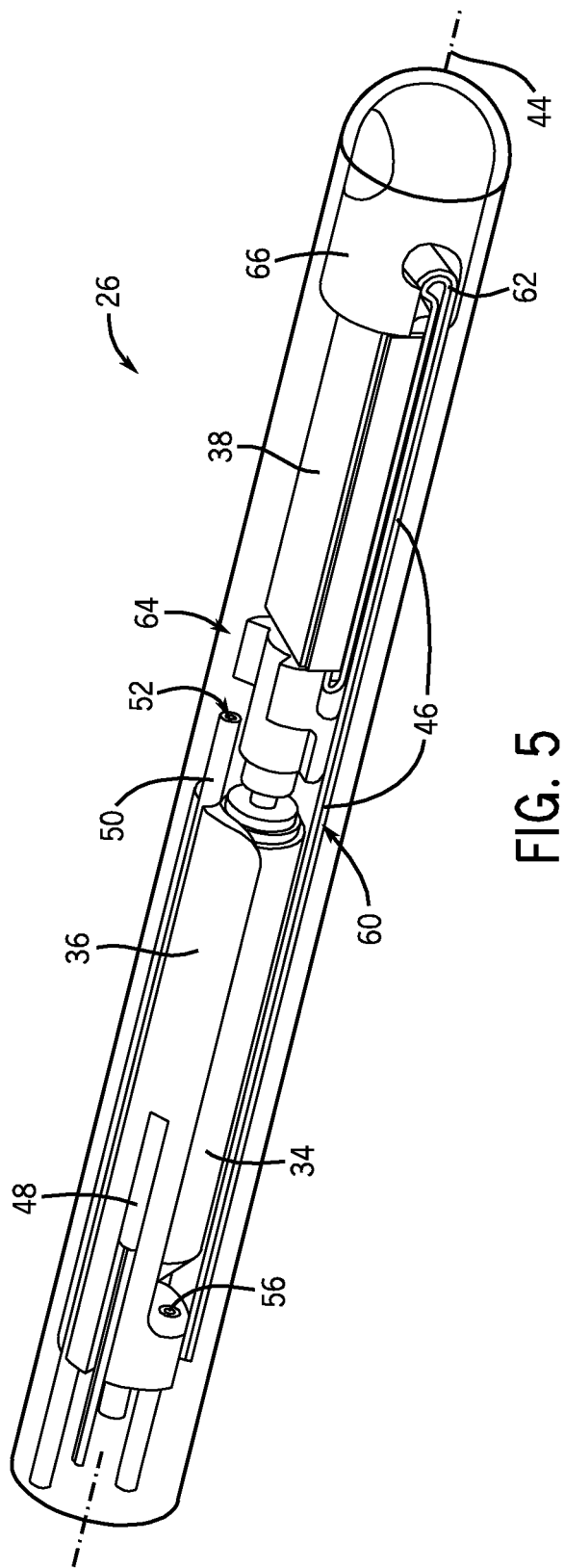
FIG. 5 is a perspective side view of yet another exemplary embodiment of an imaging catheter tip, in accordance with aspects of the present technique.

FIG. 5 is a perspective side view of yet another exemplary embodiment of an imaging catheter tip 26. This illustrated embodiment is conceptually similar to the embodiments shown in FIG. 3. However, in this embodiment, the unconstrained length of the flexible interconnect cable 46 has been increased. This increase in the unconstrained length of the flexible interconnect cable 46 may reduce the torque load on the motor 34 which may, in turn, reduce the power required. In addition, the longer flexible interconnect cable 46 may allow for a larger range of motion (e.g., accommodating a 180 degree sweep of the transducer 38) without significantly increasing the load on the motor 34.

The increase in the unconstrained length of the flexible interconnect cable 46 may be achieved by separating the flexible interconnect cable 46 from the proximal portion of the transducer assembly. In one embodiment, as shown in FIG. 5, the flexible interconnect cable 46 may be connected to the transducer 38 at the proximal and distal ends of the transducer 38. In this embodiment, the portion of the interconnect cable 46 that is attached to the proximal end of the transducer 38 is doubled over or bent back and attached along the bottom of the transducer 38 to the distal end. In other embodiments, the flexible interconnect cable 46 may be connected to the side(s) or bottom of the transducer 38 and extended along the transducer 38 to the distal end. At point 62 near the distal end of the transducer 38, the flexible interconnect cable 46 may be doubled over or bent back and attached. The interconnect cable 46 may then be unattached, flexible, and free to rotate for the full length from point 62 to the proximal end of the motor holder 36. Because only the portion of the flexible interconnect cable 46 that is attached to the transducer 38 and/or transducer holder 40 is constrained, the doubled back portion of the flexible interconnect cable 46 under the transducer 38, as well as the portion of the flexible interconnect cable 46 under the motor 34, is unconstrained and may move freely as the transducer 38 oscillates. Therefore, in this embodiment, an unconstrained length of the flexible interconnect cable 46 may be allowed to translate and rotate from point 62 all the way to the proximal end of the imaging catheter tip 26. This may both substantially increase the rotational freedom of the transducer 38 as well as substantially reduce the power required and the temperature generated by the motor 34.

As illustrated, the flexible interconnect cable 46 may not be constrained by the transducer holder 40 in the same manner as the embodiments shown in FIGS. 3 and 4. Rather, two discrete fixtures—a proximal transducer fixture 64 and a distal transducer fixture 66—may hold the transducer 38 in place. The distal transducer fixture 66 may be bonded to the distal end of the transducer 38 and may include features to hold the flexible interconnect cable 46 in place while the proximal transducer fixture 64 may include part of the hard stop mechanism.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging catheter tip, comprising:
    a housing;
    a transducer assembly located within the housing in a distal portion of the imaging catheter tip, wherein the transducer assembly comprises a transducer;
    a motor located within the housing in a proximal portion of the imaging catheter tip, wherein the motor is configured to facilitate oscillation of the transducer of the transducer assembly about a longitudinal axis of the imaging catheter tip;
    a fill tube disposed between the motor and the housing, wherein the fill tube is configured to deliver acoustic coupling fluid to the distal portion of the imaging catheter tip, wherein the fill tube is configured to restrict the oscillation of the transducer of the transducer assembly about the longitudinal axis of the imaging catheter tip; and
    a motor holder circumferentially surrounding the motor along the longitudinal axis, wherein the motor holder is configured to fix the motor in a specific position within the housing.

2. The imaging catheter tip of claim 1, wherein the fill tube is configured to deliver the acoustic coupling fluid near a proximal end of the transducer.

3. The imaging catheter tip of claim 1, wherein the fill tube is configured to deliver the acoustic coupling fluid near a distal end of the transducer.

4. The imaging catheter tip of claim 1, comprising a vent at a distal end of the transducer assembly for venting air remaining in the distal portion of the imaging catheter tip through the proximal portion of the imaging catheter tip after filling the distal portion of the imaging catheter tip with acoustic coupling fluid.

5. The imaging catheter tip of claim 4, comprising a vent tube for disposing of the vented air through the proximal portion of the imaging catheter tip.

6. The imaging catheter tip of claim 1, comprising a flexible interconnect cable disposed between the motor and the housing, wherein the flexible interconnect cable is configured to connect to the transducer.

7. The imaging catheter tip of claim 6, wherein the flexible interconnect cable is also disposed between the transducer assembly and the housing.

8. The imaging catheter tip of claim 7, wherein the flexible interconnect cable extends from the proximal portion of the imaging catheter tip to a location distal to the transducer assembly, is doubled over or bent back, and extends back to the proximal end of the transducer.

9. The imaging catheter tip of claim 1, wherein the acoustic coupling fluid is delivered at a site where the imaging catheter tip is to be used.

10. The imaging catheter tip of claim 1, wherein the acoustic coupling fluid is delivered within twelve hours of use.

11. The imaging catheter tip of claim 1, wherein the acoustic coupling fluid is delivered after manufacture and shipping of the imaging catheter tip.

12. The imaging catheter tip of claim 1, wherein the motor holder is configured to at least partially block the acoustic coupling fluid from flowing from the distal portion of the imaging catheter tip into the proximal portion of the imaging catheter tip.

13. The imaging catheter tip of claim 1, wherein the motor holder is configured to distribute heat from the motor across a longitudinal length of the imaging catheter tip.

14. The imaging catheter tip of claim 1, wherein the motor holder comprises an anisotropic or composite material having high thermal conductivity in a longitudinal direction parallel to the longitudinal axis of the imaging catheter tip, and low thermal conductivity in transverse directions perpendicular to the longitudinal axis of the imaging catheter tip.

15. The imaging catheter tip of claim 1, comprising a thermistor for monitoring the temperature of the motor.

16. A system, comprising:
an imaging system for collecting imaging data; and
an imaging catheter, comprising:
an imaging catheter tip, comprising:
a transducer assembly located in a distal portion of the imaging catheter tip;
a motor assembly located in a proximal portion of the imaging catheter tip, wherein the motor assembly is configured to facilitate oscillation of transducers of the transducer assembly;
a fill tube configured to fill the distal portion of the imaging catheter tip with fluid from a proximal end of the imaging catheter tip, wherein the fill tube is configured to restrict the oscillation of the transducers of the transducer assembly; and
a motor holder circumferentially surrounding the motor assembly along a longitudinal axis of the imaging catheter tip, wherein the motor holder is configured to fix the motor assembly in a specific position within the imaging catheter tip.

17. The system of claim 16, wherein the motor holder is configured to at least partially block the fluid from flowing from the distal portion of the imaging catheter tip into the proximal portion of the imaging catheter tip.

18. The system of claim 16, wherein the motor holder is configured to distribute heat from the motor assembly across a longitudinal length of the imaging catheter tip.

19. The system of claim 16, wherein the motor holder comprises an anisotropic or composite material having high thermal conductivity in a longitudinal direction parallel to the longitudinal axis of the imaging catheter tip, and low thermal conductivity in transverse directions perpendicular to the longitudinal axis of the imaging catheter tip.

20. The system of claim 16, comprising a thermistor for monitoring the temperature of the motor assembly.

21. An imaging catheter tip, comprising:
a housing;
a transducer assembly located within the housing in a distal portion of the imaging catheter tip, wherein the transducer assembly comprises a transducer;
a motor located within the housing in a proximal portion of the imaging catheter tip, wherein the motor is configured to facilitate oscillation of the transducer of the transducer assembly about a longitudinal axis of the imaging catheter tip;
a fill tube configured to fill the distal portion of the imaging catheter tip with fluid from a proximal end of the imaging catheter tip, wherein the fill tube is configured to restrict the oscillation of the transducer of the transducer assembly; and
a flexible interconnect cable configured to connect to the transducer at a proximal end of the transducer, wherein the flexible interconnect cable extends from the proximal portion of the imaging catheter tip to a location distal to the transducer assembly, is doubled over or bent back, and extends back to the proximal end of the transducer.

22. The imaging catheter tip of claim 21, comprising a motor holder circumferentially surrounding the motor along the longitudinal axis, wherein the motor holder is configured to fix the motor in a specific position within the housing.

23. The imaging catheter tip of claim 22, wherein the motor holder is configured to at least partially block the fluid from flowing from the distal portion of the imaging catheter tip into the proximal portion of the imaging catheter tip.

24. The imaging catheter tip of claim 22, wherein the motor holder is configured to distribute heat from the motor across a longitudinal length of the imaging catheter tip.

25. The imaging catheter tip of claim 22, wherein the motor holder comprises an anisotropic or composite material having high thermal conductivity in a longitudinal direction parallel to the longitudinal axis of the imaging catheter tip, and low thermal conductivity in transverse directions perpendicular to the longitudinal axis of the imaging catheter tip.

* * * * *